United States Patent
Margolin et al.

(10) Patent No.: US 8,997,748 B2
(45) Date of Patent: Apr. 7, 2015

(54) DILATOR ASSEMBLY, A DEVICE FOR FACILITATING TRACHEOSTOMY AND METHODS OF MAKING A PERCUTANEOUS TRACHEOSTOMA

(75) Inventors: Gregory Margolin, Stockholm (SE); Jonas Karling, Bromma (SE)

(73) Assignee: SafeTrach AB, Sundbyberg (SE)

( * ) Notice: Subject to any disclaimer, the term of this patent is extended or adjusted under 35 U.S.C. 154(b) by 201 days.

(21) Appl. No.: 13/386,265

(22) PCT Filed: Jul. 23, 2010

(86) PCT No.: PCT/EP2010/060746
§ 371 (c)(1),
(2), (4) Date: Jan. 20, 2012

(87) PCT Pub. No.: WO2011/012554
PCT Pub. Date: Feb. 3, 2011

(65) Prior Publication Data
US 2012/0138064 A1 Jun. 7, 2012

(30) Foreign Application Priority Data
Jul. 31, 2009 (EP) ..................................... 09167009

(51) Int. Cl.
*A61M 16/00* (2006.01)
*A61M 16/04* (2006.01)

(52) U.S. Cl.
CPC ................................. *A61M 16/0472* (2013.01)

(58) Field of Classification Search
USPC ............. 128/200.24, 200.26, 204.18, 207.14, 128/207.29; 606/185, 198, 130
See application file for complete search history.

(56) References Cited

U.S. PATENT DOCUMENTS

| 3,511,243 | A | 5/1970 | Toy ................................ 128/305 |
| 5,217,007 | A | 6/1993 | Ciaglia ..................... 128/207.29 |
| 2007/0289595 | A1* | 12/2007 | Lubelski .................. 128/207.14 |
| 2008/0295848 | A1 | 12/2008 | Karling et al. ........... 128/207.29 |
| 2009/0090357 | A1* | 4/2009 | Schwartz et al. ........ 128/200.26 |
| 2009/0312784 | A1 | 12/2009 | Tupper .......................... 606/191 |

FOREIGN PATENT DOCUMENTS

| WO | WO 2007/018472 A1 | 2/2007 |
| WO | WO 2008/009943 A1 | 1/2008 |

OTHER PUBLICATIONS

International Search Report and Written Opinion, PCT/EP2010/060746, mailed Oct. 11, 2010.

* cited by examiner

*Primary Examiner* — Rachel Young
(74) *Attorney, Agent, or Firm* — Winston & Strawn LLP

(57) ABSTRACT

A dilator assembly for percutaneous dilatational tracheostomy includes a dilator element having a wall and a proximal end part extending into a distal tip part via an intermediate part. The wall has a substantially U-shaped cross section defining a dilator opening. The assembly extends towards the distal tip part. The dilator assembly is part of a tracheostomy device. The device has a first branch for arranging inside the trachea, and a second branch co-operative with the first branch. The first branch has a first end and a receiving member while the opposing second end has a first coupling part. The second branch has a first end with a guide for a neck penetration member and an opposing second end with a second coupling part for coupling with the first coupling part of the first branch. The first and second branches are detachably coupled together at their respective second ends.

14 Claims, 14 Drawing Sheets

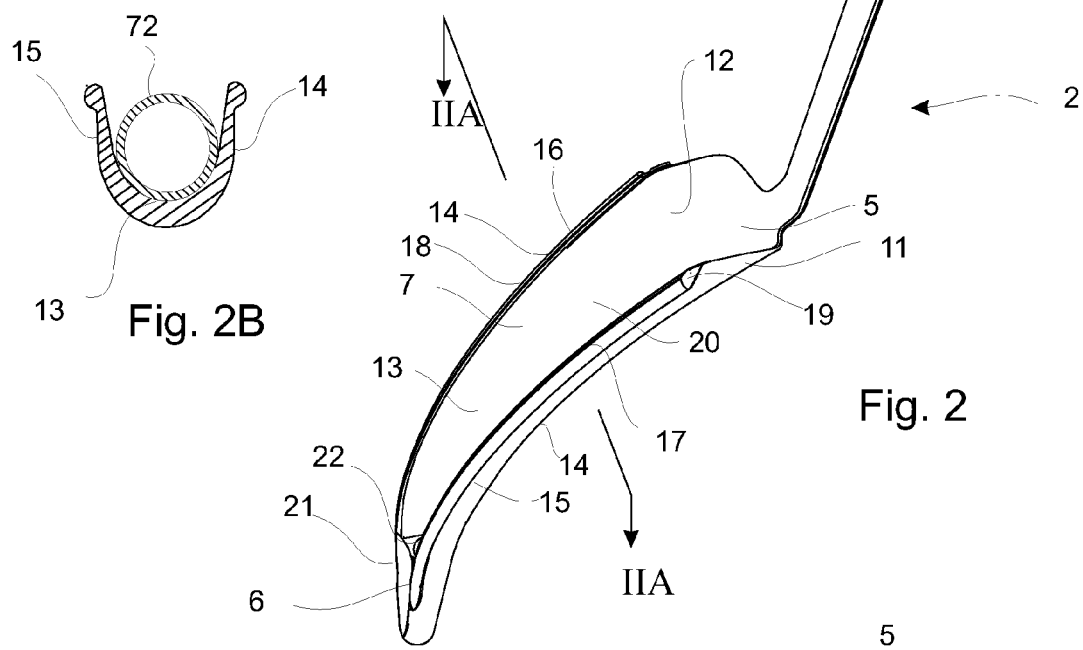
Fig. 2A
Fig. 2B
Fig. 2
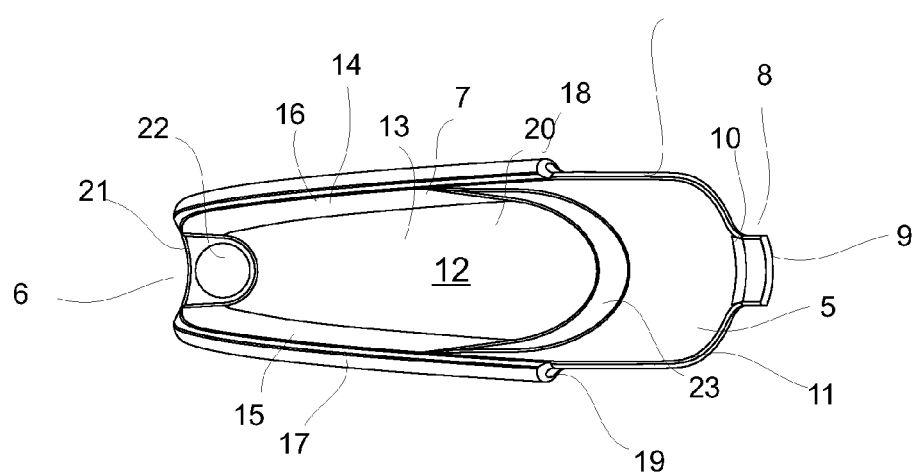
Fig. 3

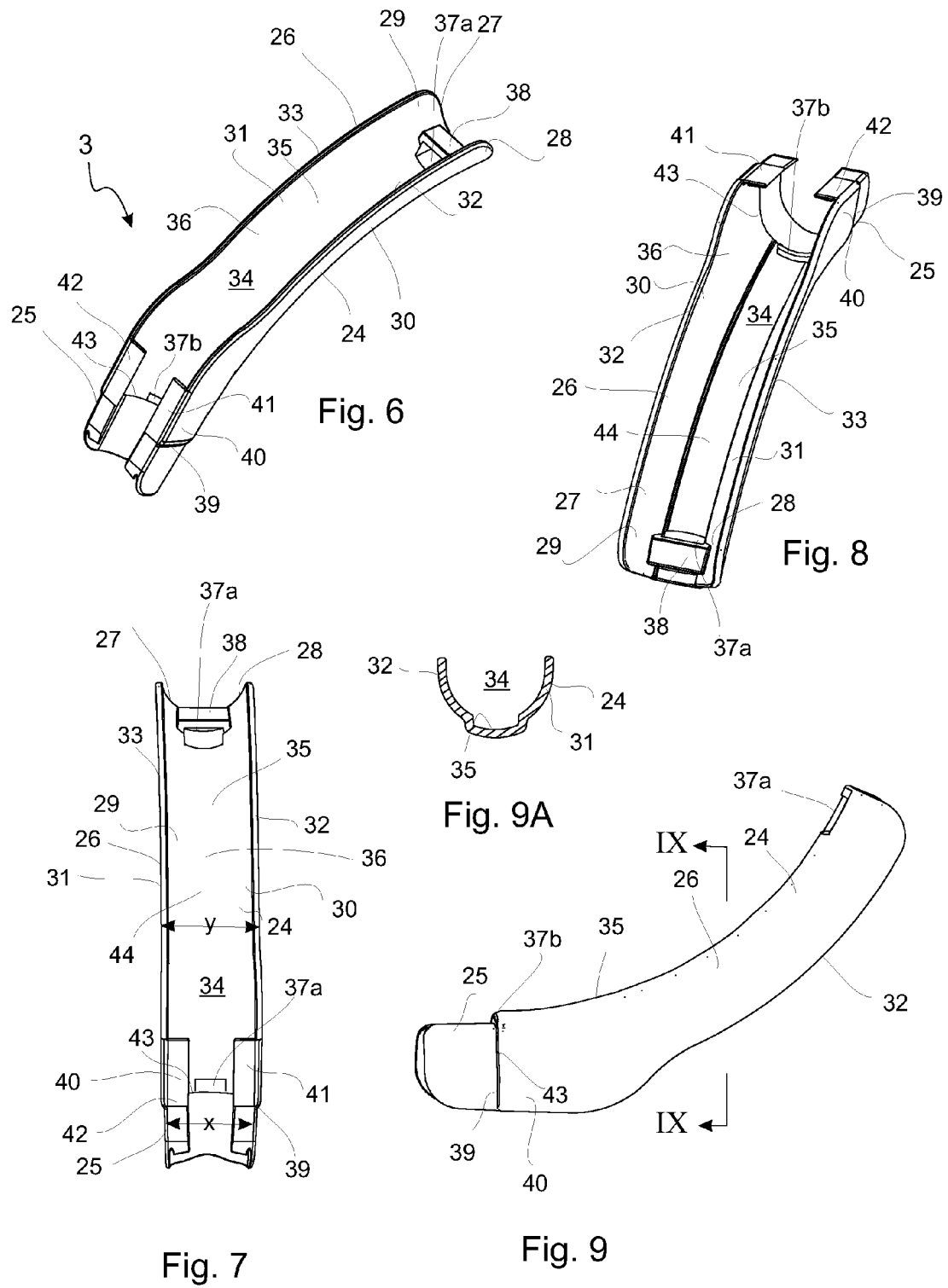

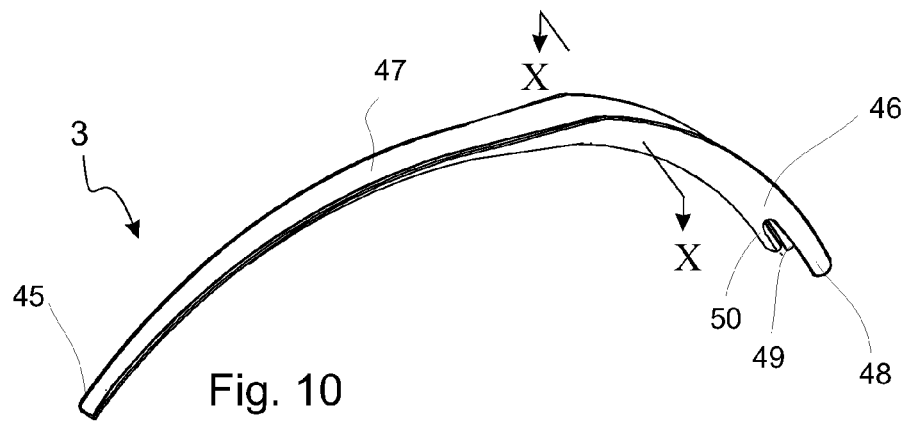
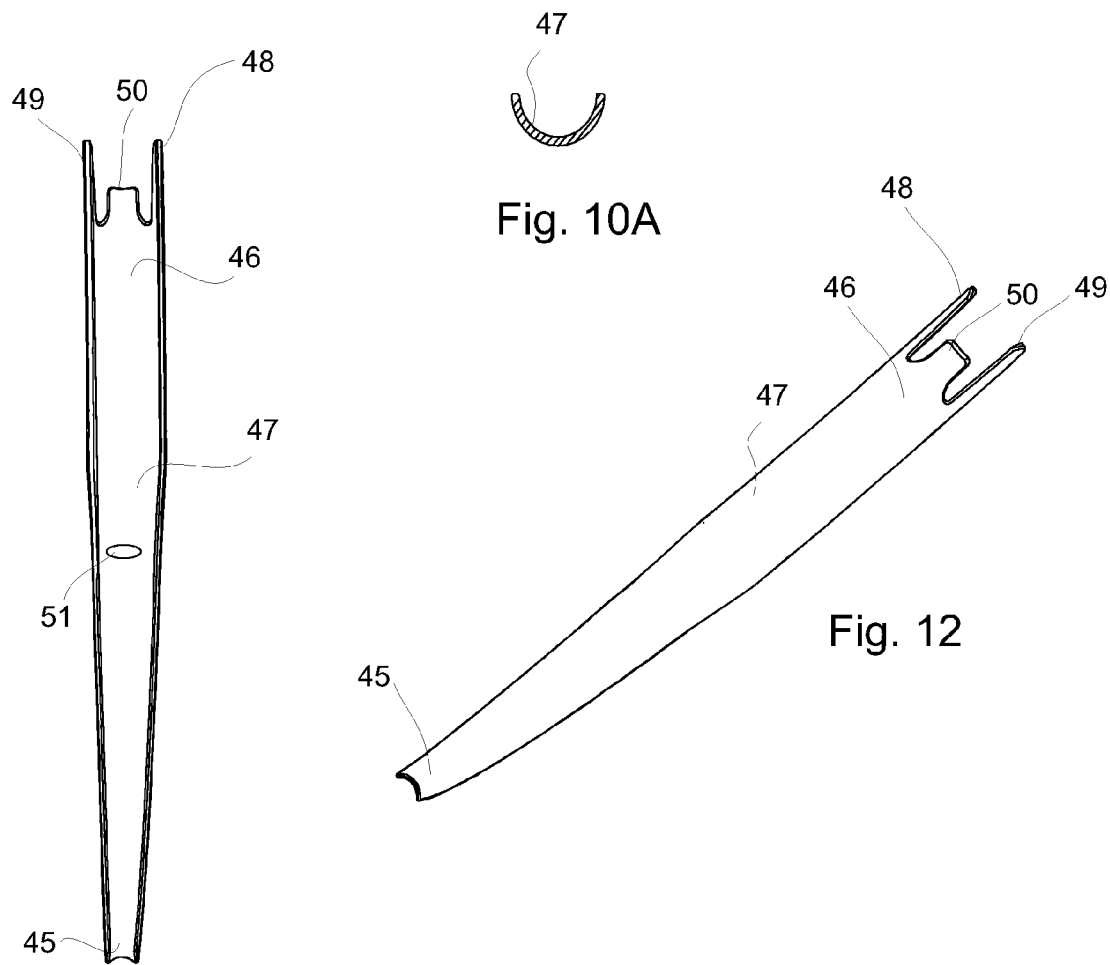

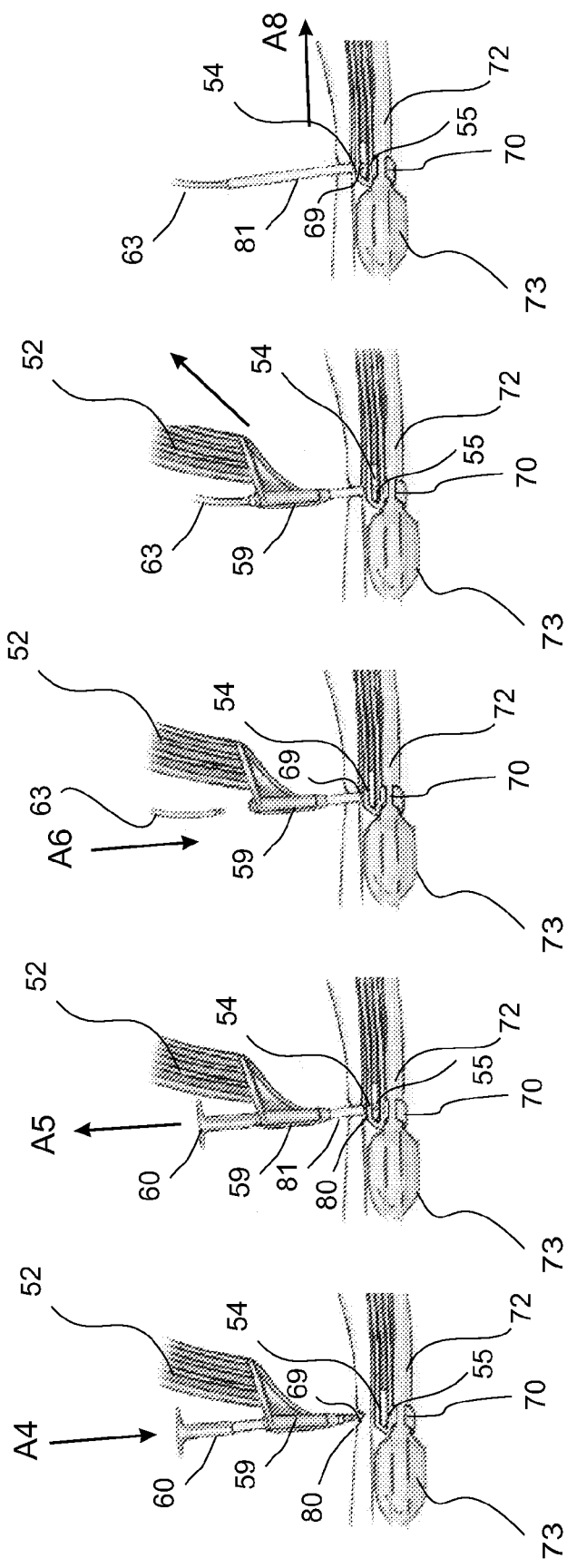

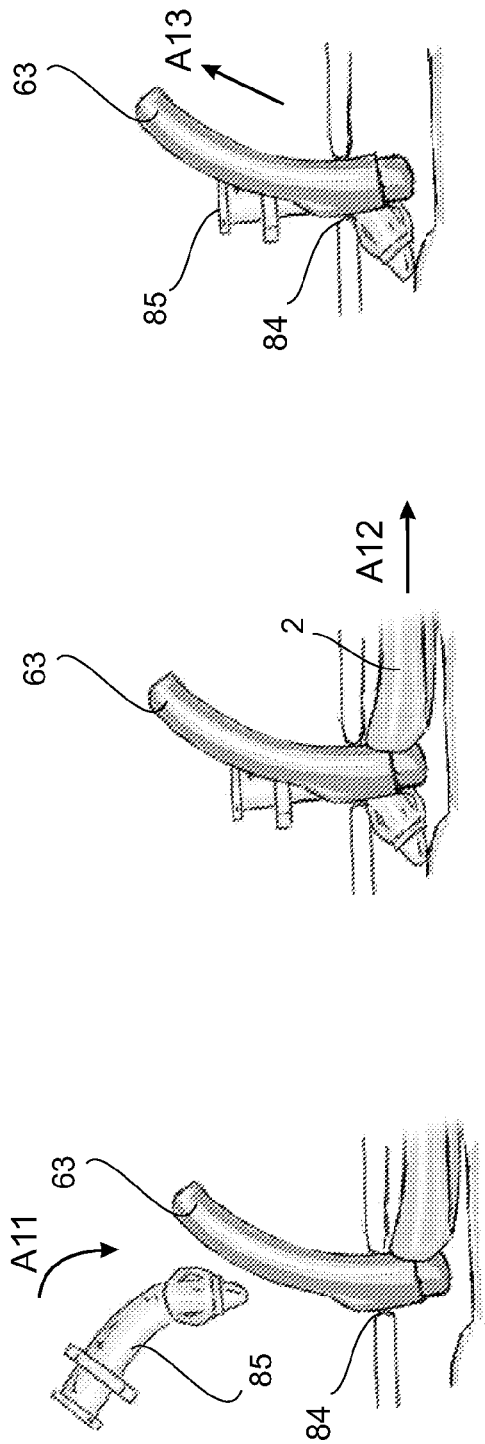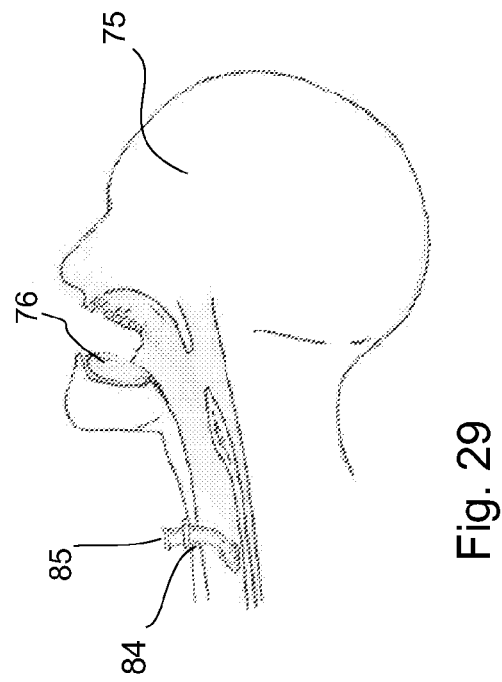

DILATOR ASSEMBLY, A DEVICE FOR FACILITATING TRACHEOSTOMY AND METHODS OF MAKING A PERCUTANEOUS TRACHEOSTOMA

This application is a 371 filing of International Patent Application PCT/EP2010/060746 filed Jul. 23, 2010.

BACKGROUND

The present invention relates to a dilator assembly adapted for percutaneous dilatational tracheostomy in a patient already having an endotracheal tube for ventilation, the dilator assembly comprising a dilator element having a wall and a proximal end part extending into a distal tip part via an intermediate part.

A tracheostomy is a surgical procedure to create an opening through the neck into the trachea. A tube is placed through the opening to provide an airway and to remove secretions from the lungs. This tube is called a tracheostomy tube or trach tube.

A tracheostomy is done in case of impaired respiratory function. This might be the case if for example a large object blocks the airway, the patient has an inherited abnormality of the larynx or trachea, has breathed in harmful material such as smoke, steam, or other toxic gases, suffers from diseases that otherwise affect breathing, e.g. severe neck or mouth injuries, or by paralysis of the muscles that affect swallowing. About 15% of the patients treated in intensive care units need a tracheostomy. The most common indications in this group are need for long-term ventilation, deteriorated pulmonary function and difficulties in weaning from respirator treatment.

Existing techniques for performing percutaneous tracheotomy procedure include making a curvilinear skin incision between sternal notch and cricoid cartilage and placing a plastic cannula and needle with fluid filled syringe attached into trachea. Aspiration of air confirms correct placement of the tip in the trachea. Next the needle is removed and the hollow cannula is left in place to enable insertion of a soft tipped guide wire into trachea through the bore of the hollow cannula. The cannula is removed leaving the guide wire in place and tracheal dilatation is undertaken using suitable means. Finally, after appropriate dilatation the tracheostomy tube is inserted with concomitant withdrawal of the endotracheal tube and ventilator tubing is connected.

Preferred dilatation procedures nowadays may follow the Ciaglia techniques, either using the Ciaglia Blue Dolphin or the Ciaglia Blue Rhino from Cook.

Ciaglia Blue Dolphin uses balloon dilatation. Ciaglia Blue Rhino is a single large tapered dilator with a soft, pliant tip and curved contours. The conical Ciaglia Blue Rhino dilator is advanced over a plastic guidewire reinforcement to enlarge the opening in the trachea. Both Ciaglia techniques are well reputed but can only be performed by very skilled staff. Moreover, they all include a plurality of steps before the tracheostomy procedure is finalised and the trach tube is placed properly. For further discussion of the known techniques for tracheostomy references are made to the applicant's International patent application no WO2007/018472.

When performing a percutaneous tracheotomy with all existing techniques, there is a risk of serious surgical complications e.g. damaging the posterior tracheal wall, large neck blood-vessels and fractures of tracheal rings.

Thus there is a need within the art for simple techniques for performing tracheostomy procedures fast and in a safe manner.

International patent application no. WO2008/09943 discloses a tracheostomy dilator for use with a guide wire in a single dilator step. This known tracheostomy dilator is curved along its length. Is has a tapering patient end region at one end and an oppositely curved handle region at its opposite end. A passage extends rearwardly along the dilator from its patient end and opens on a side of the dilator at an opening in the handle region. The passage is blocked rearwardly of the opening by an insert with a forward ramp surface, which directs a guidewire. In use one end of the guidewire projects from the patient end of the dilator and its opposite end extends along the outside of the handle region. Due to a.o. the prerequisite guide wire this known dilator cannot be used when the patient already has an endotracheal tube for ventilation. Such an endotracheal tube needs to be removed first at the risk of the patient is without respiration for the subsequent period while the tracheostoma is created. Moreover the tracheostomy dilator would take up considerable space if arranged next to an endotracheal tube and be difficult to maneuver without the endotracheal tube gets dislocated.

U.S. Pat. No. 3,511,243 discloses an apparatus for use in emergency tracheotomy, which apparatus suffers from some of the same and additional disadvantages as the above described tracheostomy dilator according to WO2008/09943. The apparatus comprises a flexible leader member for insertion through a hollow needle into the tracheal lumen, an expanding adapter apparatus detachably engaging one end of the leader member, said expanding adapter apparatus including an outer O-shaped tapered guide conduit member formed with an expanding slot and an inner expanding adapter element telescopically arranged in the outer guide conduit to extend outwardly therefrom, a cutting edge extending rearwardly from the outer guide conduit extremity. The expanding slot of the O-shaped tapered guide conduct is employed to hold a tube or other instrument in place by means of a tool inserted through the expandable slot while the O-shaped tapered guide conduit member is removed by means of a radially protruding handle the same way is was inserted. This known apparatus cannot be inserted if an endotracheal tube already is inserted in the trachea, a.o. due to the presence of the cutting edge that might damage the endotracheal tube, the large diameter of between one to one and a half inch, and the spatial hindrance if an endotracheal tube already is present.

An improved device for making a tracheotomy is known from the applicant's International patent application no. WO2007/018472. This device provides a novel surgical instrument assembly by means of which a tracheotomy can be made at lesser risk of complications and very fast. An endotracheal tube with an inflatable cuff close to the tip is inserted into the trachea. The cuff is inflated at the appropriate location just below larynx. A first branch of the instrument is guided into the trachea alongside the endotracheal tube leaving a second branch exterior to the patient and a part of the first branch inside the trachea. The second branch is hinged to the first branch at a distance from the tips of the branches, e.g. in a scissor-like or tweezer-like manner, enabling the tip of the second branch to be moved towards the tip of the first branch to puncture the neck tissue and the anterior wall of the trachea. The tip of the first branch may have a countermeasure or backstop, such as a stop plate, for preventing through puncture of the posterior tracheal wall when the tip of the second branch are swung towards the neck for penetration of the anterior tracheal wall and making the puncture. After successful puncture the second branch is swung aside and the first branch is removed from the trachea the same way it was inserted, namely through the mouth. Dilatation is then made and a tracheostomy tube is arranged into the dilated hole.

While this novel procedure discloses a plurality of advantageous feature over the prior art the inventor and applicant still aim for improving the surgical procedure towards simplified and safer techniques that can be made very fast. The faster respiration ability is restored the lower risk of brain damages. Faster and simpler procedures will save more lives.

SUMMARY OF THE INVENTION

It is a main aspect of the present invention to provide an improved and reliable dilator assembly of the kind mentioned in the opening paragraph.

It is second aspect of the present invention to provide a dilator assembly of the kind mentioned in the opening paragraph which can be inserted unobstructed into the trachea in a smooth operation.

In a third aspect according to the present invention is provided a dilator assembly of the kind mentioned in the opening paragraph which requires a minimum of steps when making a tracheostomy.

In a fourth aspect according to the present invention is provided a dilator assembly of the kind mentioned in the opening paragraph enabling making a tracheostomy at minimal risk of injuring the posterior wall of the trachea and larynx.

In a fifth aspect according to the present invention is provided a dilator assembly of the kind mentioned in the opening paragraph which do not require use of guidewires.

In a sixth aspect according to the present invention is provided a device for facilitating safe and fast tracheostomy.

In a seventh aspect according to the present invention is provided a dilator assembly of the kind mentioned in the opening paragraph which can be removed through the mouth after being introduced via an incision in the neck.

In a eighth aspect according to the present invention is provided a device and a dilator assembly of the kind mentioned in the opening paragraphs the operation of which utilises an already inserted endotracheal tube.

Within the scope of the present invention the term dilator is used for a surgical instrument or medical implement used to induce dilation or dilatation, that is to expand an opening or passage made in the anterior neck wall to create a tracheostoma.

Within the scope of the present invention the term retractor is used for a surgical instrument used to hold back the edges of an incision, in particular hold back the edges of the dilated incision to enable insertion of a trach tube.

The novel and unique whereby these aspects are achieved according to the present invention is that at least the wall of the proximal end part of the dilator element has a substantially U-shaped cross section defining a dilator opening along at least the length of the proximal end part, which dilator opening is dimensioned for receiving the already inserted endotracheal tube.

For percutaneous tracheostomy dilatation the dilator element is passed through an initial small incision made in the anterior neck wall between two adjacent tracheal rings. The dilator element is then forced onwards into the incision to enlarge it until a suitable size for insertion of a tracheostomy tube is reached. An endotracheal tube is already provided for ventilating the patient until the tracheostomy tube is correctly placed. The endotracheal tube occupies a substantial part of the very limited tracheal space making it hard to find sufficient space to manipulate a conventional dilator without withdrawing the endotracheal tube so that the tip of the endotracheal tube is above the level of tracheostomy. This is dangerous because there is a risk that the endotracheal tube might get above the vocal cord level accidentally extubating the patient and thus loosing air-way in a critical moment.

According to the present invention the endotracheal tube fits into the cavity defined by the U-shaped cross section of at least the wall of the proximal end part of the dilator element. The endotracheal tube passes via the longitudinal dilator opening between the legs of the U down into the cavity of the U along at least the length of the proximal end part and conveniently also along at least some of the length of the intermediate. In this way the major parts, in particular the widest parts, of the dilator element do not take up much extra space in the trachea. The proximal end part and optionally also the intermediate part of the dilator element are thus configured with a lengthwise furrow or cavity into which an endotracheal tube can be gradually accommodated during percutaneous dilatational tracheostomy. At least the proximal end part and optionally also the intermediate part of the dilator element partly enclosing the endotracheal tube to allow the dilator element to be slidably guided along the length of the endotracheal tube instead of being located side by side with the endotracheal tube without the endotracheal tube is available as a guide. By keeping the dilator element in close and partly enclosing contact with the endotracheal tube the risk of injuring surrounding tissue can be reduced. Accordingly, the endotracheal tube is advantageously utilised as a guide for the dilator assembly to control unintended lateral and intended forward movement of the dilator element.

As mentioned above it is preferred that the wall of the intermediate part of the dilator element also has a substantially U-shaped cross section to enable a larger length of the dilator element to partly enclosing the endotracheal tube during the percutaneous dilatational tracheostomy. Optionally, also the wall of the distal tip part has a substantially U-shaped cross section.

The thickness of the wall of the dilator element is selected as thin as possible depending on the nature of the selected material without compromising the degree of rigidity that is needed to provide the dilator element with the dimensional stability required to make a satisfactory dilation.

The interior face of at least the interior and/or exterior wall of the proximal end part of the dilator element may be provided with a friction reducing coating, layer or surface to advance the dilator element along the endotracheal tube smoothly, unobstructed and fast. Alternatively, the dilator element may be made of a material having an inherent friction reducing ability.

In the present application the term "radius of curvature" is used to characterize the measure of how curved, or bent, a given curve or surface is.

In the preferred embodiment at least the proximal end part of the dilator element and/or the intermediate part is curved along it's length at a radius of curvature which is the same or different. The radius of the curvature is shorter along the bottom of the U-shaped cross section of the wall of the dilator element than along the dilator opening. In this way the free end of the proximal end part is bend towards the distal tip part to expose the lengthwise opening for engaging and accommodating the endotracheal tube. Due to the selected degree of curvature the dilator element is able to turn during dilation to follow the neck anatomy of the patient.

When the dilator element is introduced via the incision the bended curvature of the proximal end part will allow the distal tip part of the dilator element to turn from an initial position substantially perpendicular to the neck to a turned position where at least the proximal end part encloses or partly encircles the endotracheal tube, which turned position is reached guided by the endotracheal tube without injuring tracheal tissue.

If also the intermediate part of the dilator element is curved the distal tip part of the dilator element turns earlier than if only the proximal end part is curved. The distal tip part may also be curved and the radius of curvature of any of the proximal end part, the intermediate part and the distal tip part may be the same or different. In the preferred embodiment the radius of curvature of the proximal end part is smaller than or the same as the radius of curvature of the intermediate part. The distal tip part may have a radius of curvature even smaller or none. Within the scope of the present invention only the intermediate part may be curved so that the free end of the proximal end part and the distal tip part are brought closer to each other along the bottom of the U.

In an advantageously embodiment at least a part of the dilator element tapers from the proximal end part towards the distal tip part. Preferably the dilator element tapers along the entire length of the dilator element, thus the size of the cross section of the U decreases towards the distal tip part.

The dilator assembly may further comprise a retractor element co-operative with the dilator element, preferably pivotable coupled to the proximal end part of the dilator element. The retractor element serves to keep the edges of the dilated incision spaced apart and the dilated incision open and dilated until the tracheostomy tube can be inserted. Thus, the retractor element is temporary left in the dilated artificial ventilation opening in the neck and the trachea, the tracheostoma, to prevent collapse of said ventilation opening.

To ensure that the dilator element and the retractor element can co-operate and be manipulated as an integral unit the proximal end part of the dilator element may have a first coupling means for coupling together with second coupling means on the retractor element.

A first end part of the retractor element is arranged for engaging the proximal end part of the dilator element while an opposing second end part protrudes towards a free end. The second coupling means of the retractor element for coupling with the first couplings means of the dilator element may be provided on the first end part and/or the second end part of the retractor element. The first coupling means may e.g. be a protruding strap for coupling together with the second coupling means on the retractor element, e.g. holes or eyes in the encircling wall of the retractor element's respective first and second end parts.

The first and second coupling means interlock during forward advancing of the combined dilator element and retractor element, which first and second coupling means advantageously may be designed to be releasable upon activation of a release mechanism, simply by manipulation of the first and second coupling means, or in response to a defined level of force application.

Similar to the design of the dilator element at least a lengthwise part of the wall of the retractor element may have a substantially U-shaped cross section thereby defining a retractor opening along at least a part of the length of the retractor element.

In addition to the other advantages mentioned above for the dilator element, the lengthwise openings of the dilator element and the retractor element respectively, also provide for a limited but preferred radial flexibility that enables the dilator element to self-fit over the endotracheal tube for use of the endotracheal tube as a tracheal guide during dilation, and use of the retractor element to keep the artificial opening, the tracheostoma, distended and the edges of the stoma retracted without compromising the respective dilating and retracting capabilities. No guide wires are needed for directing and controlling the dilator element.

Since the retractor element may follow the dilator element a distance into the trachea for dilation at least a part of the length of the retractor element may be curved, preferably at least the second end part.

To ensure that the dilator element and the retractor element can be operated as an integral unit the dilator assembly may further comprise a stabiliser element for structurally stabilising the combined dilator element and retractor element during percutaneous dilatational tracheostomy. The stabiliser element may simply be a shoehorn-shaped element to be inserted via the lengthwise openings along the length of the dilator element and attached retractor element, that is inside their U-shaped cavities, to prevent the proximal end part of the dilator element attached to the first end part of the retractor element to pivot too early during the dilation step. Moreover, the stabiliser element provides the combined dilator assembly with sufficient structural integrity to allow the part of the dilator assembly protruding from the incision to serve as a handle thereby offering the operator a good grip and expedient working conditions, enabling the operator to act fast and without hesitation.

The legs of the substantially U-shaped cross sections of any of the proximal end part, the distal tip part, the intermediate part and/or the retractor element of the dilator assembly may be substantially parallel or diverge to facilitate receiving the endotracheal tube inside the elongated cavity or furrow defined by the legs of the U and to facilitate smooth displacement of the dilator assembly along the endotracheal tube.

It should be understood from the above description and discussion of the dilator assembly that the distal tip part of the dilator element includes the tip of the dilator element and the part of the dilator element initially passed into the incision to approach and engage the endotracheal tube. Thus in a typical embodiment of a dilator assembly the distal tip part typically is dimensioned to reach from the exterior of the neck to below the endotracheal tube already inserted in the trachea for ventilation of the patient. The length of the proximal end part of the dilator element includes or corresponds substantially to the part of the dilator element configured for coupling together with the retractor element. The intermediate part of the dilator element extends between the distal tip part and the proximal end part. The curved length of the distal tip part and the proximal end part of the dilator element may typically be about 10-20% of the entire curved length of the dilator element at the respective ends of said dilator element. For example in case of a dilator element having a curved length of e.g. about 15 cm, the distal tip part and the proximal end part may each be e.g. 2 cm, making the intermediate part 11 cm. Dilator assemblies may be provided in various sizes with different lengths of distal tip part, proximal end part and intermediate part for use with patient of various neck sizes.

The invention further relates to a device for facilitating tracheostomy.

The device is of the kind comprising
a first branch for arranging inside the trachea,
a second branch co-operative with the first branch for creating a tracheostoma,
the first branch has a first end to be introduced into the trachea, which first end has a receiving means, and an opposing second end provided with a first coupling part,
the second branch has a first end with a guide means for a neck penetration means, and an opposing second end with a second coupling part for coupling with the first coupling part of the first branch, and the first branch and the second branch are detachable coupled together at respective second ends.

According to the present invention this device further comprises a dilator assembly adapted for percutaneous dilatational tracheostomy in a patient already having an inserted endotracheal tube for ventilation, the dilator assembly comprising a dilator element having a wall and a proximal end part extending into a distal tip part via an intermediate part. At least the wall of the proximal end part of the dilator element has a substantially U-shaped cross section defining a dilator opening along at least the length of the proximal end part, which dilator opening is dimensioned for receiving the already inserted endotracheal tube.

The above-described additional components and features of the dilator element according to the present invention can be implemented in the dilator assembly according to the present invention either alone or in various combinations to at least arrange the retractor element and/or the proximal end part of the dilator element in the dilated incision subsequent to dilation made using said dilator element.

In the preferred embodiment according to the present invention the distal tip of the dilator element is provided with a line, which line has a free end with a first engagement means, and the first end of the first branch has a second engagement means for engaging the first engagement means of the line, when the first engagement means has been inserted into the trachea through the guide means of the second branch.

For use in the present context the term "line" means any flexible and bendable elongate member, such as a thin tube, a wire, a mesh or a rope or similar means that can be used to secure the first engagement means to the distal tip part of the dilator element at a distance suitable for at least reaching through the guide means prior to starting dilation. The length of the line may for example correspond to the length of the first branch, but can within the scope of the present invention be shorter or longer than the first branch.

In a simple embodiment the first engagement means is a male part, such as a barb with an enlarged head, and the second engagement means is a female part, such as a hole with a smaller diameter than the widest diameter of the barb to ensure firm engagement. The male part and the female parts may interlock in a disengageable manner. When pulling the line a pulling force is applied to the second engagement means of the first branch that catches the first engagement means of the dilator assembly. The result of the pulling action is that the first engagement means is retracted inside the trachea via the initial incision and further along the endotracheal tube, which fits into the U-shaped cavity of the dilator element, thereby bringing along the dilator element. When retracting the dilator assembly through the incision, the incision is automatically dilated. Dilation may or may not be assisted by pushing the dilator element inside the incision from outside the neck. The retractor element, which is pivotally coupled to the dilator element, is also retracted until till first end part of the retractor element is located in the dilated incision. The receiving means may be configured with the first engagement means or simply serve both the engaging function and the backstop function.

No subsequent manipulation, such as using supplemental tool, is required because the size of the opening corresponds to the size of the cross section of the first end part of the retractor element, which then again is selected to fit the selected tracheostomy tube. The dilator element is arranged to decouple the retractor element. Once the dilator element and the first end part of the retractor element have been retracted inside the trachea the retractor is pivoted away from the dilator element and thus safely anchored in the trachea. The first coupling means and the second coupling means are disengaged, and the dilator element can now be fully retracted via the mouth by means of the first branch hooking the line. The retractor element is left in the tracheostoma for subsequent placing of the tracheostomy tube. The procedure can also be done the reverse way, performing the placement of the tracheostomy tube first, disconnecting the retractor from the dilator secondly and finishing by taking away the retractor and dilator.

The invention also relates to a method for making a percutaneous tracheostoma using the device for facilitating tracheostomy described above with or without a retractor element.

The method is of the kind comprising the steps of
(a) introducing the first branch into the trachea via the mouth along an endotracheal tube to position the receiving means between tracheal rings and the first coupling part of the first branch outside the patient,
(b) coupling the second coupling part of the second branch together with the first coupling part and arranging the guide means above the receiving means,
(c) introducing a penetration means through the guide means and the anterior tracheal wall until the guide means are stopped by the receiving means, to make an incision, and removing the penetration means,
(d) introducing the first engagement means through the incision either together with the penetration means or after removal of the penetration means and coupling the first engagement means together with the second engagement means,
(e) decoupling the second branch and the first branch and removing the second branch, and
(f) retracting the first branch a distance out of the trachea bringing the dilator assembly along until a retractor element or the proximal end part of the U-shaped dilator element is located inside the incision dilated by the dilator element.

The method further comprises that
(g) the dilator element and the retractor element are decoupled from each other and the first branch and the dilator element is retracted from the trachea via the mouth leaving the retractor element in the dilated incision.

The method may further comprise that
(h) an optional stabiliser used for holding the retractor element and the dilator element together is removed, and the retractor is pivoted with the dilator element left in the trachea.

In an alternative embodiment the method comprises an alternative method step (g') substituting step (g), wherein step (g') the dilator element is inserted via the mouth and retracted from the trachea via the incision resulting in dilation.

Additional method steps according to the present invention include in the following order or in other order one or more of the steps that
(i) the endotracheal tube is retracted until the tip of the endotracheal tube is visible through the retractor element or the dilator element,
(j) that a tracheostomy tube is inserted through the retractor element in the trachea, or in the alternative into the proximal end part of the dilator element, and
(k) ventilation is established,
(l) any of the retractor element and/or dilator element is removed.

Thereby the percutaneous dilatational tracheostomy is complete.

The percutaneous dilatational tracheostomy may according to the present invention only take a few minutes to perform.

The method for performing percutaneous dilatational tracheostomy is, according to the present invention, particular easy and fast to perform if a stabiliser element is used in step (f) for holding the dilator element and the retractor element together during dilation.

BRIEF DESCRIPTION OF THE DRAWINGS

The dilator assembly, the device for facilitating tracheostomy and the method for making a percutaneous tracheostoma will be explained in further details below with references to the accompanying drawing in which FIG. 2 shows the dilator element of FIG. 2 seen in perspective oblique from the lengthwise dilator opening, FIG. 2A is a cross sectional view taken along line II-II in FIG. 2, FIG. 2B corresponds to FIG. 2A where an endotracheal tube, seen in cross section, is seen inserted via the dilator opening into the cavity between the opposing walls of the dilator element, FIG. 3 is a top view of the dilator element of FIG. 2 seen along an axis extending through the distal tip part, FIG. 6 shows, seen in perspective a retractor element according to the present invention, FIG. 7 is the retractor element of FIG. 4 seen down inside the retractor opening, FIG. 8 is the retractor element of FIG. 4 seen from the second end part and into the first end part, FIG. 9 is the retractor element of FIG. 4 seen from the side, FIG. 9a is a cross sectional view taken along line II-II in FIG. 9, FIG. 10 shows the stabiliser element seen in perspective oblique from a tip part towards the opposite free end, FIG. 10a is a cross sectional view taken along line X-X in FIG. 10, FIG. 11 shows the stabiliser element of FIG. 10 down inside its lengthwise cavity and modified to include a hole in the central part, FIG. 12 is the stabiliser element of FIG. 10 viewed from the side opposite the stabiliser opening.

FIG. 16-FIG. 29 shows a series of steps for performing percutaneous tracheostomy using the dilator assembly and the device according to the present invention.

DETAILED DESCRIPTION OF THE INVENTION

Figure 1:
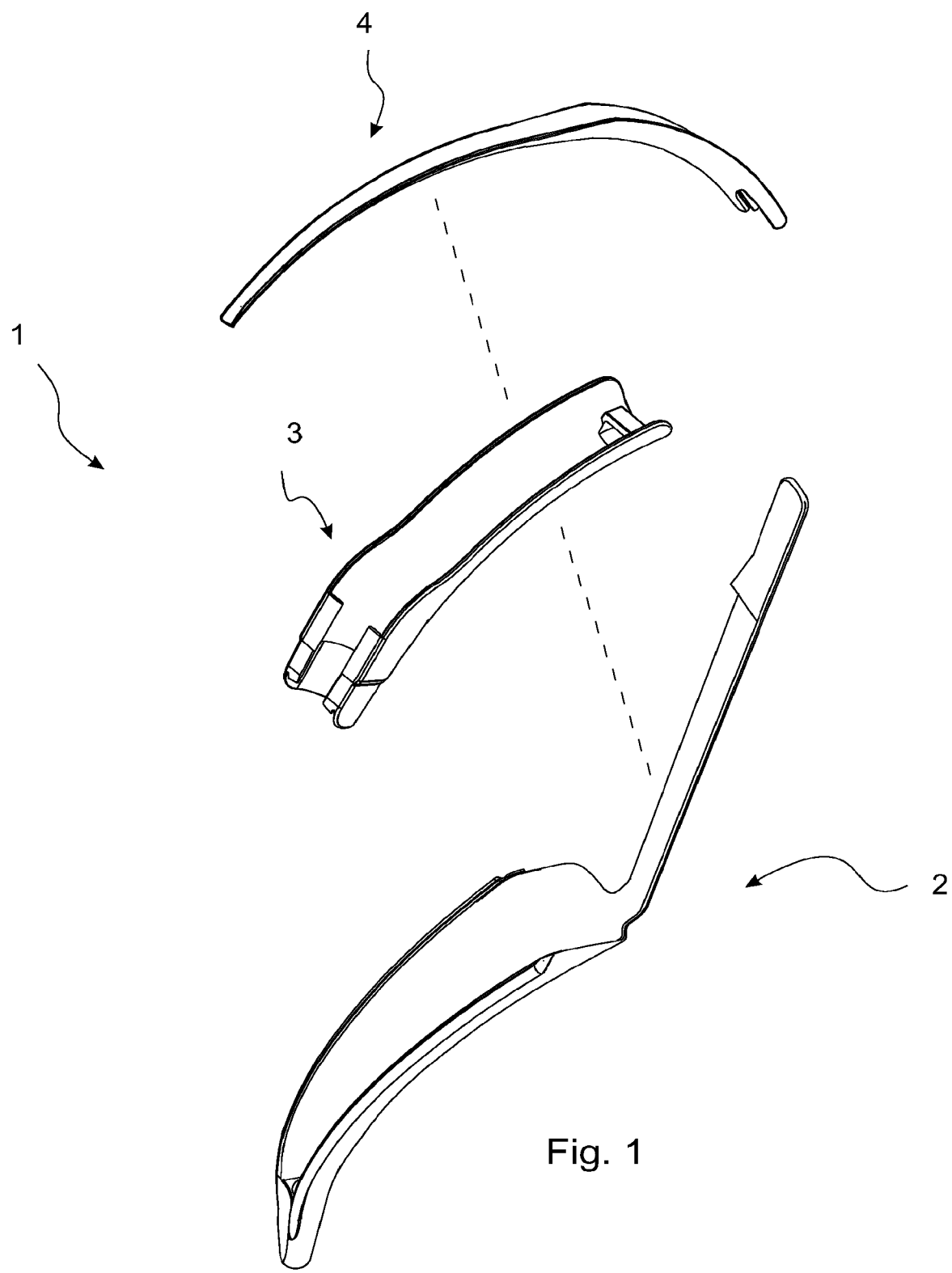
FIG. 1 shows, seen in perspective, the components for a preferred embodiment of a dilator assembly according to the present invention.

FIG. 1 shows the components for a preferred embodiment of a dilator assembly 1. The dilator assembly includes a dilator element 2, a retractor element 3 and a stabiliser element 4, the details of which will be explained in more detailed with references to the following FIGS. 1-15 in which the component are illustrated from various angles.

In FIG. 2 the dilator element 2 has a proximal end part 5, a distal tip part 6 and an intermediate part 7. The proximal end part 5 has a first coupling means 8, in the form of a protruding strap 8. The strap 8 protrudes towards a free end 9 having a protrusion 10.

As is clear from the cross sectional view taken along line II-II in FIG. 2A and 2B the wall 11 of the dilator element 2 has a U-shaped cross section, delimiting a dilator cavity or furrow at the proximal end part 5 and the intermediate part 7, which dilator cavity 12 has a U-shaped cross section. The U-shaped dilator cavity 12 has an interior bottom face 13 and opposite facing side walls 14,15 defined by the legs 14,15 of the U. The free longitudinal edges 16,17 of the side walls 14,15 is provided with rounded flanges 18,19 which however may be dispensed with. The free longitudinal edges 16,17 of the side walls 14,15 delimit a longitudinal dilator opening 20 along the proximal end part 5 and the intermediate part 7 for accommodating an endotracheal tube, as seen in FIG. 2B. The endotracheal tube, seen in cross section in FIG. 2B, is inserted via the dilator opening into the cavity 12 between the opposing walls of the dilator element. Further details will be described later with reference to the further figures.

In the embodiment for a dilator element 2 shown in FIG. 2 the distal tip part 6 has an annular wall 21 defining a bore or hole 22 for securing a pulling line (not shown).

FIG. 3 shows that at the proximal end part 5, the bottom face of the U-shaped dilator cavity 12 has a shoulder 23 protruding towards the dilator opening 20. The shoulder 23 serves as a stop for the retractor element 3 when the dilator element 2 and the retractor element 3 are joined.

Figure 4:
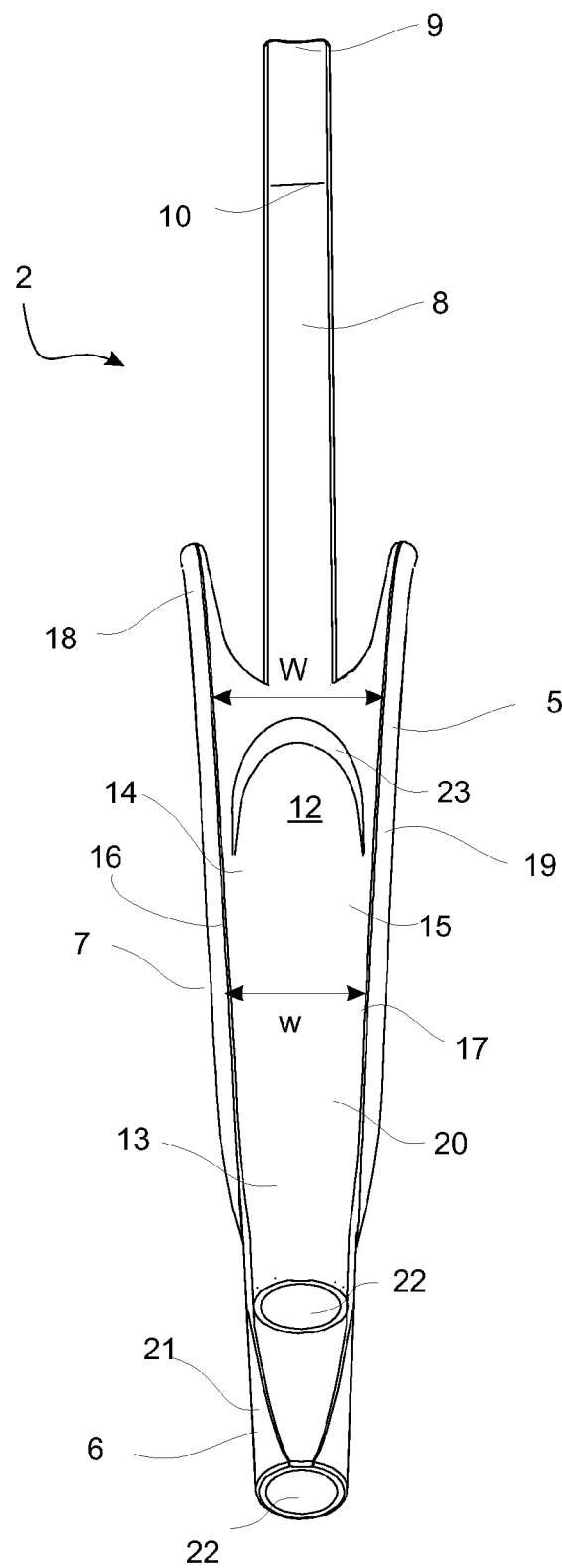
FIG. 4 is the dilator element of FIG. 2 seen down into the dilator opening.

In FIG. 4 the dilator element is seen along its length and down into the dilator opening 20 to illustrate that the dilator element 2 tapers towards the distal tip part 6. Especially the proximal end part 5 and the intermediate part 7 tapers gradually towards the distal tip part 6. Thus the U-shaped cross section gets smaller and smaller. Accordingly the width W between the side walls 14,15 at the proximal end part 5 is larger than the width w between the side walls 14,15 at the intermediate part 7.

Figure 5:
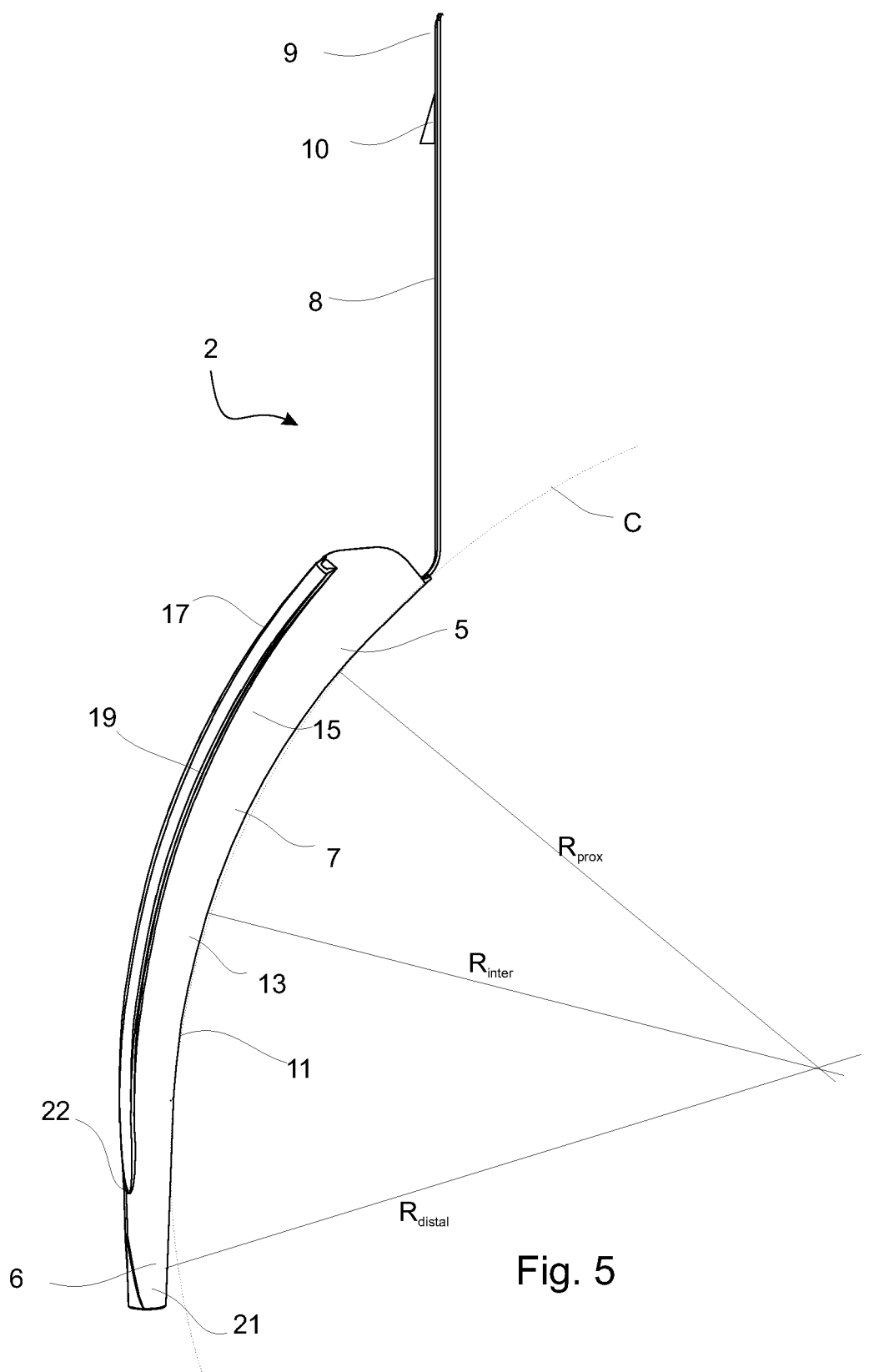
FIG. 5 is a side view of the dilator element of FIG. 2 taken in the position of FIG. 4.

In FIG. 5 the dilator element 2 is seen from the side to illustrate the radius of curvature along the length of the dilator element 2. At the proximal end part 5, the radius of curvature is $R_{prox}$, at the intermediate part 7 the radius of curvature is $R_{inter}$, and at the distal tip part 6 the radius of curvature is $R_{distal}$. As indicated by the dotted half circle C, in the embodiment of a dilator element 2 shown in FIGS. 1-5 the radius of curvature $R_{prox}$ of the proximal end part 5 is substantially the same as the radius of curvature $R_{inter}$ of the intermediate part 7. The radius of curvature $R_{prox}$ of the distal tip part 6 is however larger than both $R_{pro}$ and $R_{inter}$. The radii of curvature are indicated as examples and within the scope of the present invention other relations between radiuses of curvature are intended. For example $R_{inter}$ may be larger than $R_{prox}$, and $R_{dista}$ may be almost zero. The radius of the dilator element 2 at the dilator opening 20 is larger than at the bottom face 13.

FIG. 6 shows the retractor element 3 also shown in FIG. 1. The retractor element 3 has a wall 24 at least a length of which has a U-shaped cross section. The retractor element 3 has a first end part 25, which is arranged for engaging the proximal end part 5 of the dilator element 2, and an opposing second end part 26 that protrudes towards a free end 27. The wall 24 of the second end part 26 has a second coupling means in the form of a hole 37a at the free end 27 for passage of the free end 9 of the strap 8 of the dilator element 2. The legs 28,29 of the U define the side walls 30,31 of the retractor element 3. The free edges 32,33 of the legs 28,29 delimit a retractor opening 34 opposite the bottom face 35 of the U. Thus the U of the retractor element 3 constitutes a longitudinal retractor cavity to be arranged in elongation of the longitudinal dilator cavity 12 when joined to said dilator element 2. A further hole 37*b* through the bottom face wall 24 of the first end part 26 at the transition 43 between the first end part and the second end part 26 serves for initial passage of the free end 9 of the strap 8 of the dilator element 2 which free end 9 is externalised again through the hole 37*a* in the wall 24 of the second end part 26 until the protrusion 10 is outside the retractor cavity 36 and abuts the exterior face of the bottom face wall 24. A bridge member 38 between the side walls 30,31 extends above hole 37*a*. The bridge member 38 forms part of the second engagement means and serves to detachably engage and lock the protrusion 10 of the dilator element 2 inside the hole 37*a*, to keep the dilator element 2 and the retractor element 3 closely joined during tracheostomy. The hole 37*b* at the transition 43 may be optionally provided in the first end part 25 of the retractor element 2.

The section of the free edges 32,33 included in the first end part 25 and an adjacent section 40 of the second end part 26 have protruding webs 41,42 turned toward each other to reduce the exterior width or diameter of the retractor opening 34 and provide the first end part 25 and the adjacent section 40 of the second end part 26 with a more convenient substantially circumferential cross section to be used when the retractor element 3 is left in the dilated incision to support insertion of a tracheostomy tube.

AS seen better in the front view of FIG. 7 the first end part 25 has an exterior width x that is smaller than the exterior width y of the second end part to define a breast 39 suitable to rest on the proximal end part 5 of the dilator element 2 when the first end part 25 of the retractor element 3 is inserted into the proximal end part 5 of the dilator element 2. The breast 39 further defines a pivot axis or point for pivoting relative to the dilator element 2.

In FIG. 8 the retractor element is seen from the second end part 26 and inside the first end part 25 to illustrate the U-shaped cross section. A recess 44 is provided lengthwise in the interior face of the bottom face 35 between the holes 37*a*, 37*b* to provide an accommodation space for the strap 8 of the dilator element 2.

In FIG. 9 the retractor element 3 is seen from the side to better illustrate its curvature. The radius of curvature may be the same or different along the curved length of the retractor element. Preferably the radius of curvature of the second end part 26 is substantially the same as the radius of curvature $R_{prox}$ of the proximal end part 5 of the dilator element 2 to expose the retractor opening and arranged said retractor opening 34 in arched or bended continuity of the dilator opening 12 to define a continuous furrow of U shaped cross section, as seen in the cross sectional view of FIG. 9A.

The stabiliser element 4, shown from various angles in FIGS. 10, 11 and 12, may be used to keep the dilator element 2 and the retractor element 3 rigidly together during initial stages of dilation.

The stabiliser 4 has a tip part 45 and an opposing free end 46. The longitudinal curved body 47 of the stabiliser 4 is designed and U-shaped as a curved shoehorn that fits inside the continuous cavities 12,36 of the joined dilator element 2 and retractor element 3, to reinforce said elements, in particular at the pivoting joint at the breast 39 of the retractor element 3 during dilation and introduction through the incision in the neck intended for the tracheostoma. In order for the body 47 of the stabiliser element 4 to fit inside the cavities 12,36 it is preferred that the stabiliser 4 has substantially the same curvature as the joined dilator element 2 and retractor element 3, respectively, and a cross section that allow the stabiliser to fit between the sidewalls of both the dilator element and the retractor element. Use of a stabiliser is optional, but preferred to prevent premature pivoting of the retractor element in relation to the dilator element. Thus the stabiliser ensures that the dilator element and the retractor element remain joined until the first end part of the retractor element is located inside the dilated incision.

The free end 46 of the stabiliser 4 is divided in three spaced apart flaps, a first flap 48, a second flap 49 and a central flap 50 protruding between the first flap and the second flap and designed for being arranged through the hole 37*a* of the second end 26 of the retractor element for further holding and locking the strap 8 in the cavity 36 of the retractor element, so that the dilator element and the retractor element tightened together until release. The central flap 50 may be inserted below the bridge member 38 to restrain the stabiliser element in the cavities 12,36.

FIG. 10*a* shows a cross section taken along line X-X in FIG. 10 and illustrates the U-shaped cross section of the stabiliser element. Within the scope of the invention the term U-shaped is used to describe a shape in the form of the letter U. It is to be understood, that the distance between the legs may be different, e.g. widening or narrowing towards the free ends of the U. The height of the legs may vary and may be substantially absent, in which case the term "U-shaped" is used for the section of the circle forming the bottom of the U.

As indicated only in FIG. 11 the stabiliser element may optionally have a hole 51, to be aligned with the second hole 37*b* of the retractor element for externalisation of the strap 8 of the dilator element 2 through the dilator opening and retractor opening, in which case the strap can be held between the fingers of the operator to serve as an extra grip. The free end 10 of the strap 8 may, if suitable and the length of the stabiliser allows for it, be arranged through the hole 37*a* at the second end part 26 of the retractor element, in which case the strap 8 rests on the interior face of the stabiliser element.

If the stabiliser is made without a hole 51 the strap extend between the exterior bottom face of the stabiliser, the convex face, and the interior bottom face of the retractor element, the concave face.

Figures 13, 14:
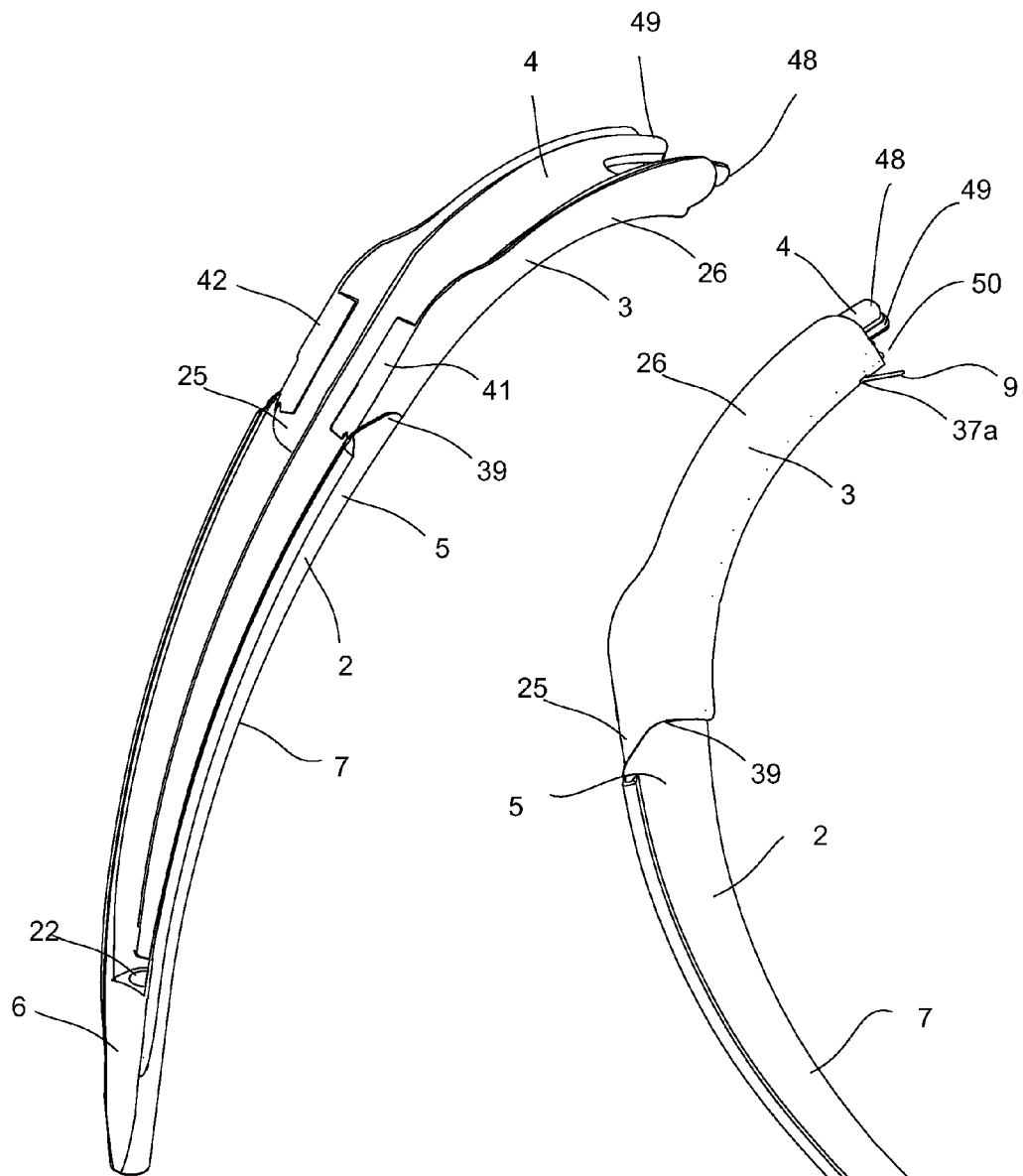
FIG. 13 illustrates in perspective the dilator assembly in the assembled state.
FIG. 14 shows the same seen from the side.

FIG. 13 illustrates in perspective the dilator assembly 1 in the assembled state where the dilator element 2 is joined to the retractor element 3 by means of the strap 8. The curvature of said joined elements 2,3 is maintained due to enforcement by the stabiliser element 4, which is inserted partly into the cavity 12 of the dilator element 2 and partly into the cavity 36 of the retractor element 3. The front end part 25 of the retractor element 3 is inserted into the proximal end part 5 of the dilator element 2 so that the breast 39 of the retractor element 3 abuts the edge of the free end of the proximal end part 5 of the dilator element 2.

The free end 9 of the strap 8 is inserted into the hole 37*a* at the first end part 25 of the retractor element 3. The central flap of the stabiliser element 4 is passed below bridge member 38 at the second end 26 of the retractor element to press the tip 45 of the dilator element 4 towards the distal tip part 6 of the dilator element 2 and catching the strap between the stabiliser element and the retractor element.

In FIG. 14 is shown a side view of an assembled dilator assembly 1. The strap 8 is passed through the hole 37*a* at the second end of the retractor element 3, as described previously. FIG. 14 also shows the curvature of the dilator assembly when the dilator element 2, the retractor element 3 and the stabiliser element 4 are firmly joined.

Figure 15:
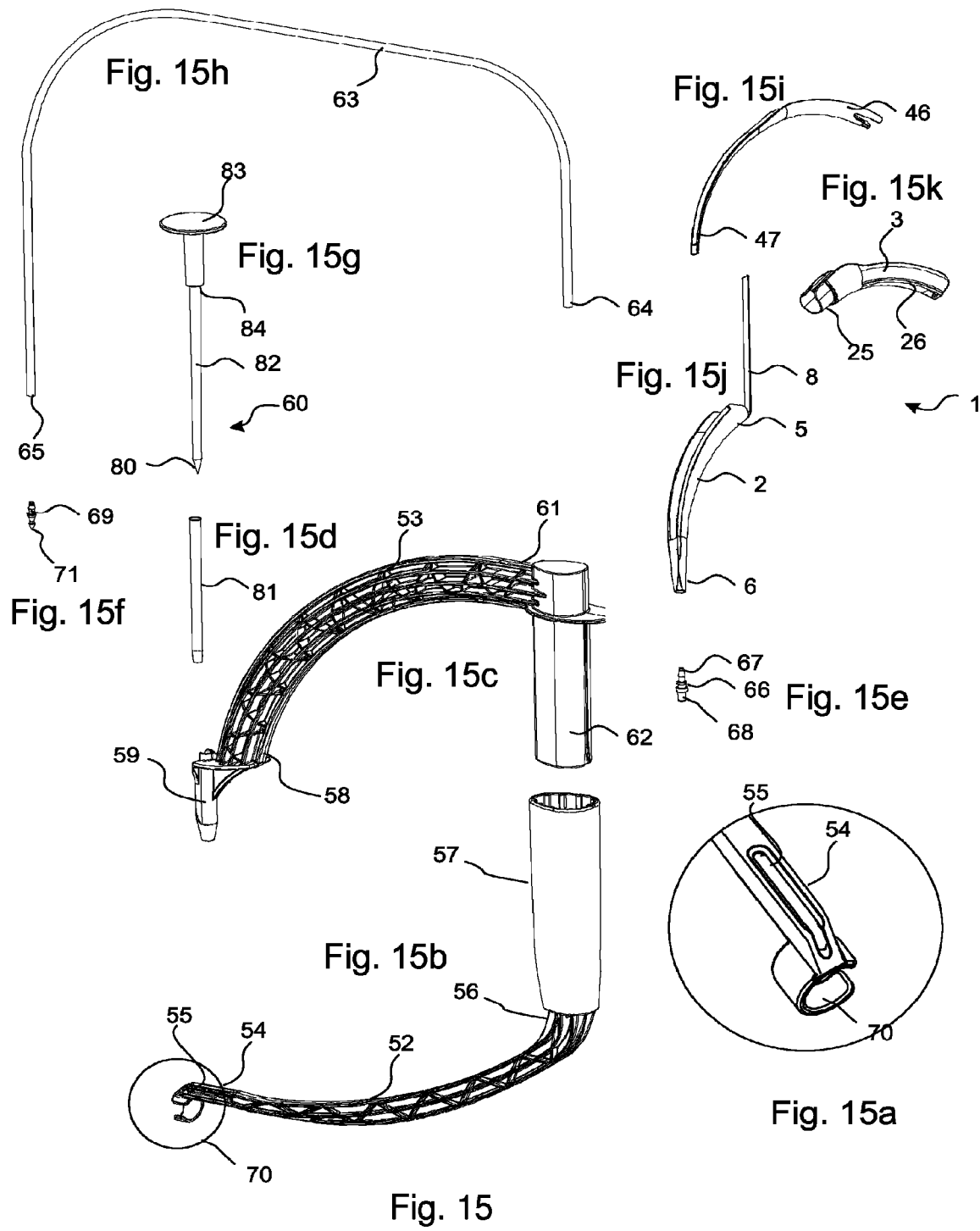
FIG. 15 shows the components of a device for facilitating tracheostomy, FIG. 15a-FIG. 15k each identify a component of FIG. 15, which shows a device for facilitating tracheostomy.

The device for facilitating tracheostomy shown in FIG. 15 has a first curved branch 52 for arranging inside the trachea, a curved second branch 53 co-operative with the first branch 52 for creating a tracheostoma. The first branch 52 has a first end 54 to be introduced into the trachea, which first end 54 has a receiving means 55, and an opposing second end 56 provided with a first female coupling part 57. The second branch 53 has a first end 58 with a guide means 59 for a neck penetration means 60 and an opposing second end 61 with a second male coupling part 62 for detachable coupling with the first coupling part 57 of the first branch 52.

The dilator assembly 1 comprises the dilator element 2, the retractor element 3, the stabiliser element 4 and a line 63 having a dilator element end 64 and a penetration end 65.

When the dilator assembly 1 is attached to the line 63 a plug element 66 has a first end 67 secured inside the bore 22 of distal tip part 6 of the dilator element 2 and a second end 68 secured to the dilator end 64 of the line 63. A first engagement means 69 having a barb 71 for engaging the receiving means 55 is secured to the penetration end 65 of the line 63. Alternatively the plug element 66, the line 63, the dilator element 2 and the first engagement means 69 are moulded together as one single unit.

The first end 54 of the first branch 52 further has a tracheostomy tube slide ring 70 or other suitable slide means that are configured to slidingly engage an endotracheal tube already present in the trachea. The principle of the sliding means is described in co-pending Swedish patent application no. 0802321-0.

The first end 58 of the second branch 53 has a tube shaped guide means 59 for guiding a penetration means 60 towards the receiving means 54. The penetration means has a shaft 82 with a pointed tip 80 and an opposing head with a pressure plate 83. The shaft 82 extends into a tubular penetration guide tube 81.

The first branch and the second branch are both curved. The first branch 52 has a curvature corresponding to the curvature of the respiratory way from the mouth down into the trachea in a patient having his/hers head bend backwards to expose the tracheal rings and a length suitable for situating the receiving means between tracheal rings at the location intended for the tracheostoma. The curvature of the second branch 53 is selected to pass free of the patient's face. When the coupling parts 57,62 are coupled together the substantially tubular hollow guide means 59 is located above the receiving means 55. The penetration means 60 are placed in the guide means 59 and forced through the neck wall to make the initial incision or puncture for the tracheostomy as will be described with reference to the subsequent figures illustrating schematically a series of steps for performing percutaneous trancheostomy using the dilator assembly and device according to the present invention.

The first end 54 of the first branch 52 is seen from the front and in the enlarged scale view of FIG. 15A. The receiving means 55 is designed as a track or groove 55 serving as a backstop for the penetration means. The track or groove may also in itself constitute the second engagement means 55, which second engagement means in the alternative may be a separate component (not shown). The second engagement means 55 is dimensioned to non-detachably engage the first engagement means 69 at the penetration end 65 of the line 63, in this case a barb 71.

The first branch 52 and the second branch 53 have truss structure to preserve dimensional stability during manipulation and to make the branches lightweight. This design should not be construed to limit the invention, as the branches also can be tubular, having smooth exterior sides etc.

The method for performing percutaneous tracheostomy using the dilator assembly and the device according to the present invention will be clearer from the description of the following FIGS. 16-29.

Figure 16:
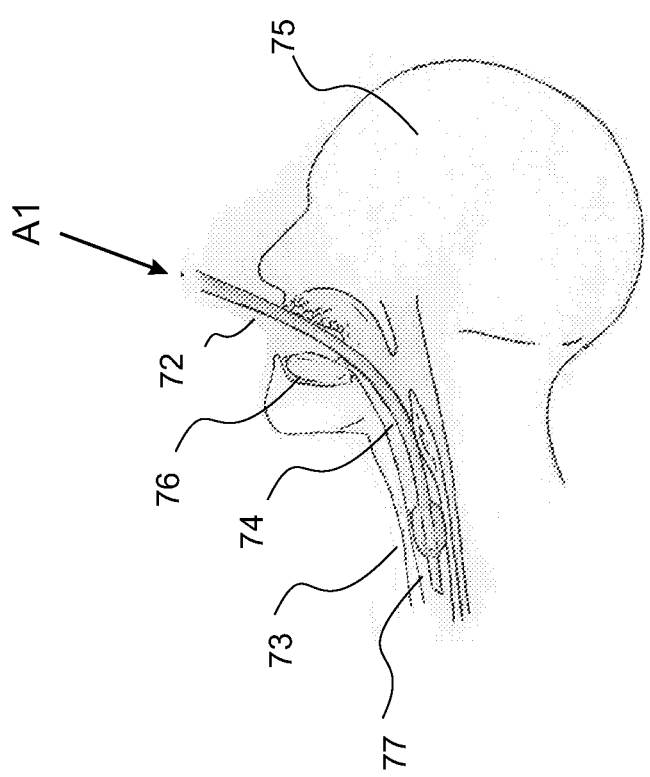
Figure 19:
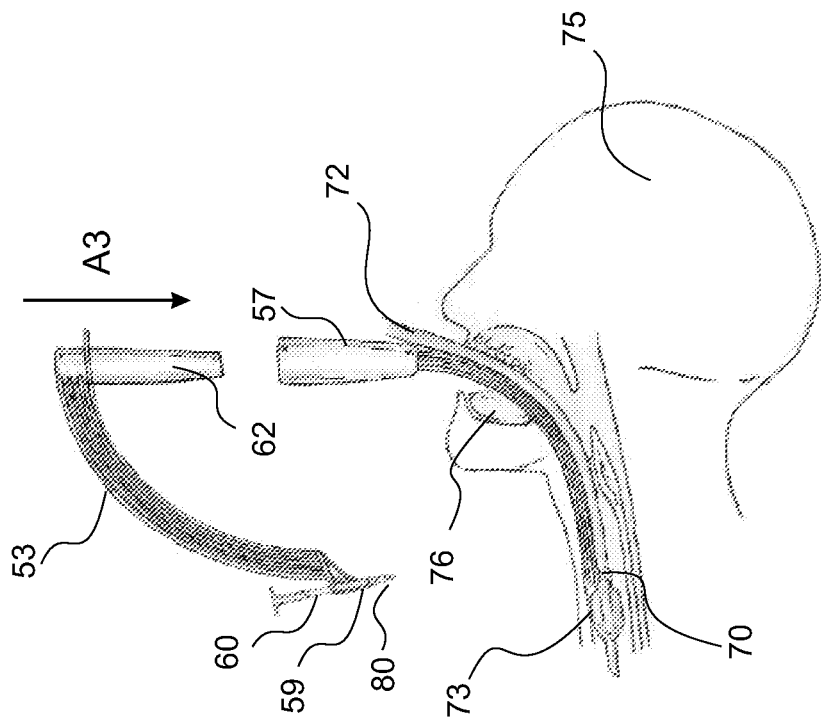

In FIG. 16 the patient 75 has been anesthetized and muscle relaxed. The neck is slightly stretched and an endotracheal tube 72 having an inflatable cuff 73 is inserted into the trachea 74 through the patient 75's mouth 76, as indicate with the arrow A1, so that the tip 77 of the endotracheal tube 72 and the inflated cuff 73 is located so that incision or penetration can be made between the first and second or second and third tracheal cartilage rings (not shown), depending on where the tracheostoma is to be created. The cuff 73 is inflated sufficiently to ensure dislocation when making the tracheostomy procedure. The position of the endotracheal tube 72 is controlled via a laryngoscope so that a mark on the tube corresponds with the level of the vocal cords.

Figure 17:
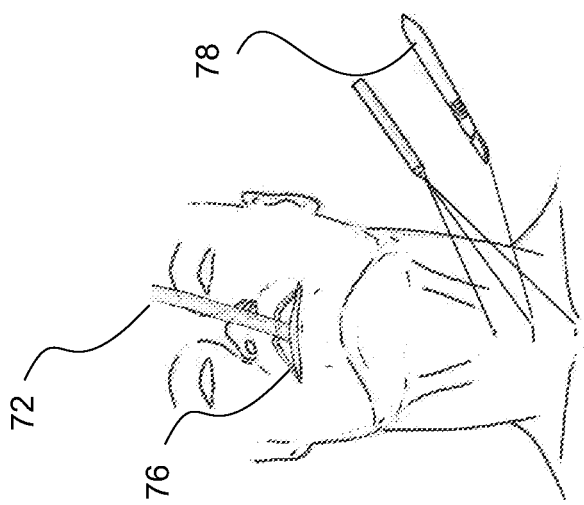

Then the neck is palpated and anatomically assessed, and the site of surgery is indicated with a marker 78 as shown in FIG. 17.

Figure 18:
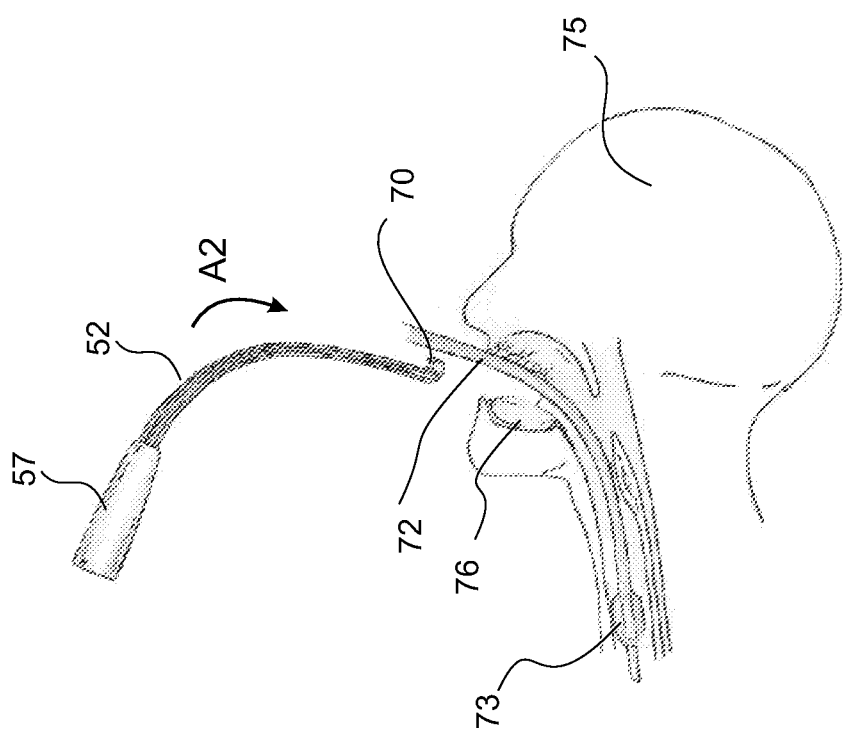
Figure 20:
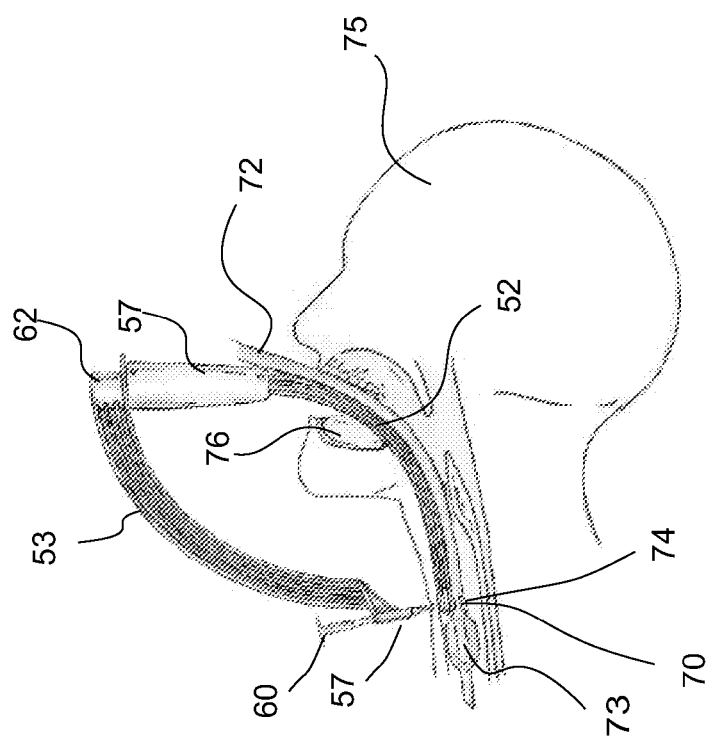

Next the slide ring 70 of the first engagement means of the inner branch 52 is attached to the endotracheal tube 72 as shown in FIG. 18. As indicated with the arrow A2 the slide ring 70 is conveyed slidingly to reach the position shown in FIG. 19 past the vocal cords, i.e. so far that the transition at the second end of the first branch 52 into the first coupling part 57 reaches a tube marker of e.g. 28 cm for an adult patient, or hits the inflated cuff 73, thereby locating the receiving means 55 of the first end 54 of the first branch 52 distanced from the vocal cords and between tracheal cartilage rings. The first coupling part 57 of the first branch 52 now protrudes from the mouth 76 of the patient 75 ready for mating with the second coupling means 62 of the second branch 53. The penetration means 60 is placed in the guide means 59 of the second branch 53, which is then moved in the direction of the arrow A3 shown in FIG. 19 to reach the joined position of the first and second coupling parts 57,62 as shown in FIG. 20.

The tip 80 of the penetration means 60 points towards the receiving means 55 of the first branch 52 inside trachea 74. In this mode internal and external references are obtained for the location of the tracheotomy. In case of unfavorable anatomical conditions, such as thick, swollen neck, the position of the receiving means 55 can be checked using a laryngoscope.

Infiltration anesthesia of the skin with intramuscular needle is carried out and an app. 20 mm transverse incision is placed through the skin and corium. Puncture is now made following the steps schematically shown in the detailed enlarged scale views of FIGS. 21a-21e.

In FIG. 21a the neck wall and tracheal wall is punctured by moving the pointed sharp tip 80 of the penetration means 60 inside the guide means 57 in the direction of the arrow A4 through the tissue layers until the tip 80 of the penetration means 60 its prevented from further advancement due to hitting the first engagement means 55 of the first branch 52 or until the lower edge 84 of the pressure plate 83 hits the guide means 59. The penetration means shaft 82 is removed from the guide means 57 in the direction of the arrow A5 seen in FIG. 21b leaving the tubular penetration guide tube 81 behind for insertion of the second engagement means 69 as indicated with the arrow A6 in FIG. 21c.

The second engagement means 69 includes a barb 71 for coupling together, with the first engagement means 55, e.g. a track or groove in the first branch 52 as shown in FIGS. 21d and 21e. The engagement of the first 55 and second 69 engagement means may elicit a click noise informing the operator of the engagement.

The second branch 53 is then detached from the tubular penetration guide tube 81 and removed in the direction of the arrow A7 in FIG. 21e.

Figure 22:
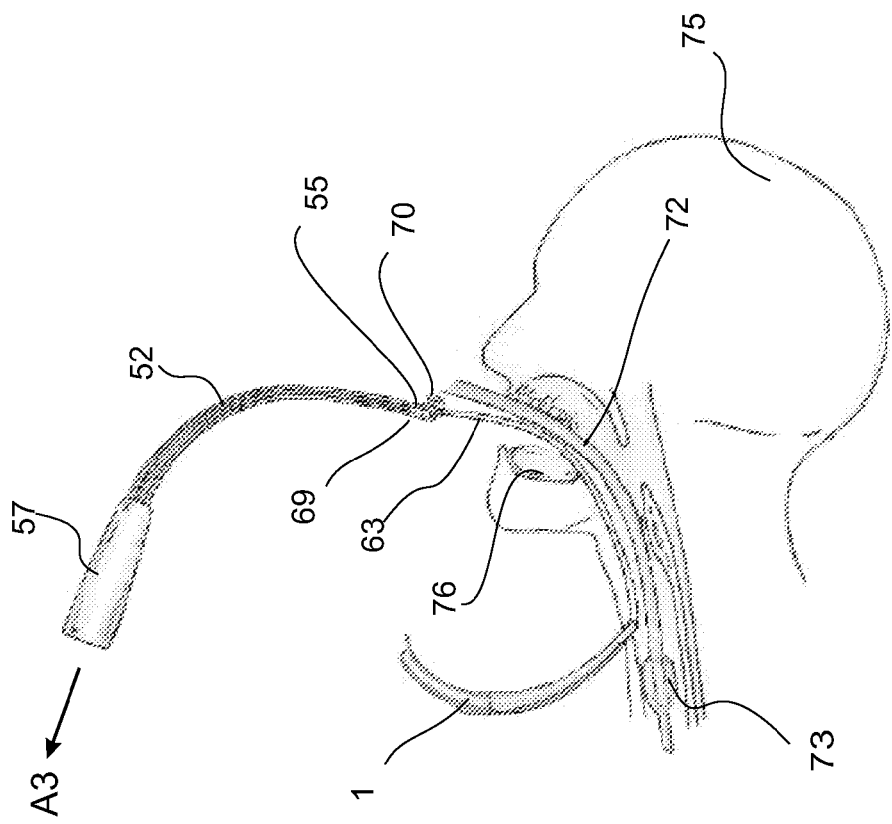

As shown in FIG. 22 the dilator assembly 1 is secured to the line 63 and the dilator assembly 1 is now retracted inside the trachea, as indicated by arrow A8 in FIG. 21d, together with the tubular penetration guide tube 81 through which the line 63 passes by gently pulling the first branch 52 out of the mouth, again by sliding along the endotracheal tube 72.

Figures 23, 24, 25:
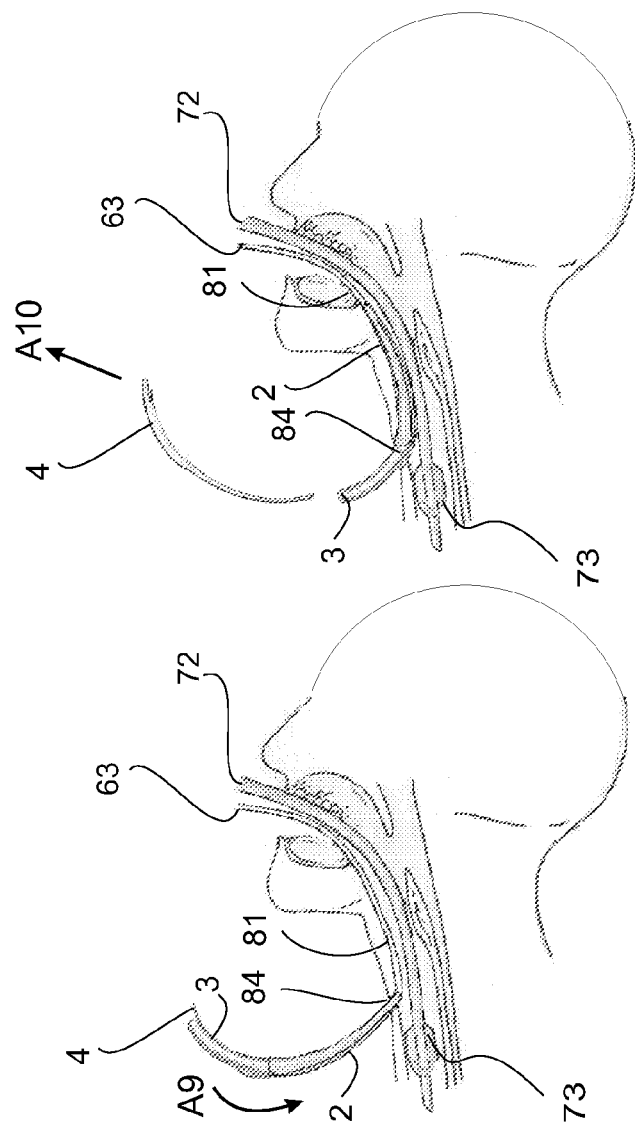

The U-shaped dilator element 2 with its stabilizer element 4 and connected retractor element 3 thereby dilates the tracheostoma 84 to desired dimension as shown in FIG. 23 when said dilator assembly components are moved into the trachea as indicated by the bend arrow A9 in FIG. 23.

When the breast 30 of the second end part 26 of the retractor element 3 reaches or passes the skin level of the neck, the stabiliser element 4 is removed in the direction of the arrow A10 as shown in FIG. 24.

As shown in FIG. 25 the retractor element 3 is then pivoted caudally until it is locked in the tracheostoma 84 and the first end part 25 of retractor element 3 is arranged substantially perpendicular to the neck. In this mode, the endotracheal tube 72 can be inspected or alternatively palpated with a finger.

The endotracheal tube 72 is un-cuffed and gently pulled out until its tip is positioned just above the first end part 25 of retractor, that is below the retractor opening and as illustrated in FIG. 26 an appropriate tracheostomy tube 85 is introduced in the tracheostoma 84, as indicated by arrow A11.

Ventilation through the tracheostomy tube 85 is established and the retractor element 3 is disconnected from the dilator element 2, which is fully removed via the mouth as indicated with the arrow Al2 in FIG. 27.

Finally the retractor element 3 is moved out of the tracheostoma 84 as indicated by the arrow A13 in FIG. 28 to leave the tracheostomy tube 85 in place in the artificial ventilation opening 84 in the neck, the tracheostoma 84, as seen in FIG. 29.

The procedure can also be done in the reverse order, in which case the retractor element is removed first and the dilator element and endotracheal tube removed in a second step.

In yet an alternative use of the device for facilitating percutaneous tracheostomy the dilator assembly is pulled inside the trachea via the mouth and out through the incision in the anterior neck wall to thereby dilate the penetrated neck wall and creating a tracheostoma.

The proximal end part serves in this embodiment as the retractor, in which case the proximal end part may be configured as a temporary insertion guide for the tracheotomy tube. By securing the first engagement means at the free end of the line of the dilator assembly to the first end of the first branch of the device for facilitating percutaneous tracheostomy, the first branch may expediently serve for positioning the first engagement means inside the trachea at the location intended for the stoma. The penetration means may include a third engagement means for engaging the first engagement means at the end of the line so that when the penetration means are withdrawn from the guide means the line will be tighten by the engaged first and third engagement means. As a result the dilator element can be retracted inside the mouth along the endotracheal tube and out through the incision for dilating said incision and subsequent installation of the tracheotomy tube.

The various ways of using the dilator assembly and device for facilitating percutaneous tracheotomy should not be seen at limiting the possibilities of making combinations and modification of the uses, and it is intended within the scope that both assembly and device can be used for other stoma making procedures using the fixed order of step, only some of the step or reordered steps of the method indicated in the description above.

What is claimed is:

1. A device for facilitating tracheostomy comprising:
a first branch for arranging inside a trachea,
a second branch co-operative with the first branch for creating a tracheostoma,
wherein the first branch has a first end to be introduced into the trachea, which first end has receiving means, and an opposing second end provided with a first coupling part,
wherein the second branch has a first end with a guide for a neck penetration member and an opposing second end with a second coupling part for coupling with the first coupling part of the first branch, and
wherein the first branch and the second branch are detachably coupled together at respective second ends, and
wherein the device further comprises a dilator assembly adapted for percutaneous dilatational tracheostomy in a patient already having an inserted endotracheal tube for ventilation, the dilator assembly comprising a dilator element having a wall and a proximal end part having a length and extending into a distal tip part via an intermediate part, wherein at least the wall of the proximal end part of the dilator element has a substantially U-shaped cross section defining a dilator opening along at least the length of the proximal end part, which dilator opening is dimensioned for engaging and accommodating the already inserted endotracheal tube.

2. The device according to claim 1, wherein the distal tip part of the dilator element of the dilator assembly is provided with a line, which line has a free end with first engagement means, and the first end of the first branch has second engagement means for engaging the first engagement means which has been inserted into the trachea through the guide of the second branch.

3. The device according to claim 2, wherein one of the first and second engagement means is a male part and the other of the first and second engagement means is a female part, which male and female parts are configured to interlock.

4. The device according to claim 1, wherein the dilator element is arranged to decouple a retractor element to leave the retractor element in situ in the tracheostoma in response to applying a pulling force in the line.

5. The dilator assembly according to claim 1 wherein at least the proximal end part or the intermediate part of the dilator element is configured to partly enclose the endotracheal tube to allow the dilator element to be slidably guided along the length of the endotracheal tube, thereby enabling use of the endotracheal tube as a guide to control unintended lateral and intended forward movement of the dilator element.

6. The dilator assembly according to claim 1, wherein the wall of the intermediate part of the dilator element has a substantially U-shaped cross section.

7. The dilator assembly according to claim 1, wherein at least the proximal end part or the intermediate part of the dilator element is curved along its length.

8. The dilator assembly according to claim 1, wherein at least a part of the length of the dilator element tapers from the proximal end part towards the distal tip part.

9. The dilator assembly according to claim 1, wherein the dilator assembly further comprises a retractor element co-operative with the dilator element.

10. The dilator assembly according to claim 9, wherein the proximal end part of the dilator element has a first coupling means for coupling together with a second coupling means of the retractor element.

11. The dilator assembly according to claim 10, wherein:
- a first end part of the retractor element is arranged for engaging the proximal end part of the dilator element,
- an opposing second end part of the retractor element protrudes towards a free end, and
- the second coupling means is provided on the first end part and/or the second end part of the retractor element.

12. The dilator assembly according to claim 9, wherein at least a lengthwise part of the wall of the retractor element has a substantially U-shaped cross section defining a retractor opening along at least a part of the length of the retractor element.

13. The dilator assembly according to claim 9, wherein at least a part of the length of the retractor element is curved.

14. The dilator assembly according to claim 9, wherein the dilator assembly further comprises a stabiliser element for stabilising the dilator element and the retractor element when the dilator element and retractor element are coupled together.

\* \* \* \* \*